United States Patent
Zare et al.

Patent Number: 6,084,682
Date of Patent: Jul. 4, 2000

[54] CAVITY-LOCKED RING DOWN SPECTROSCOPY

[75] Inventors: Richard N. Zare; Barbara A. Paldus, both of Stanford; Charles C. Harb, Palo Alto; Thomas Spence, Union City, all of Calif.

[73] Assignee: The Board of Trustees of the Leland Stanford Junior University, Palo Alto, Calif.

[21] Appl. No.: 09/061,080

[22] Filed: Apr. 15, 1998

[51] Int. Cl.[7] .................................................. G01N 21/00
[52] U.S. Cl. ............................................ 356/437; 356/440
[58] Field of Search .................................. 356/432, 437, 356/439, 440; 250/343

[56] References Cited

U.S. PATENT DOCUMENTS 5,528,040  6/1996  Lehmann .
5,815,277  9/1998  Zare .

OTHER PUBLICATIONS

Drever, R. et al. Laser Phase and Frequency Stabilization Using an Optical Resonator. Applied Physics B 31, 97–105. 1983.

Li, Z. et al., Swept–frequency induced optical cavity, Optics Communications, 86, pp. 51–57, 1991.

DeVoe, R. et al., Laser frequency division and stabilization, American Physical Society,, 1984, pp. 2827–2829.

Romanini, D. et al., Diode laser cavity ring down spectroscopy, Chemical Physics Letters, 270, pp. 538–545, 1997.

Romanini, D. et al., CW cavity ring down spectroscopy, Chemical Physics Letters, 264, pp. 316–322, 1997.

Harb, C. et al., Intensity–noise properties of injection–locked lasers, Am. Physical Soc., 54(5), pp. 4370–4382, 1996.

Engeln, R. et al., Phase shift cavity ring down absorption spectroscopy, Chemical Physics Letters, 262, pp. 105–109, 1996.

Engeln, R. et al., Polarization dependent cavity down spectroscopy, J. Chem. Phys., 107(12), pp. 4458–4467, 1997.

*Primary Examiner*—K. P. Hantis
*Attorney, Agent, or Firm*—Lumen Intellectual Property Services

[57] ABSTRACT

Distinct locking and sampling light beams are used in a cavity ring-down spectroscopy (CRDS) system to perform multiple ring-down measurements while the laser and ring-down cavity are continuously locked. The sampling and locking light beams have different frequencies, to ensure that the sampling and locking light are decoupled within the cavity. Preferably, the ring-down cavity is ring-shaped, the sampling light is s-polarized, and the locking light is p-polarized. Transmitted sampling light is used for ring-down measurements, while reflected locking light is used for locking in a Pound-Drever scheme.

19 Claims, 4 Drawing Sheets

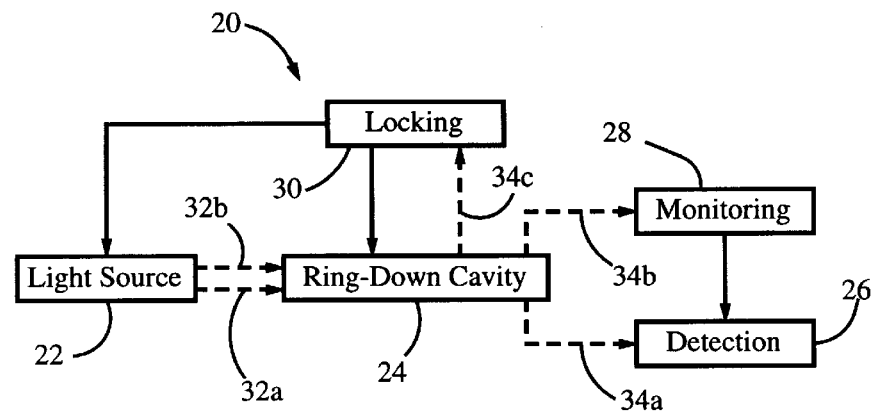
FIG. 1-A
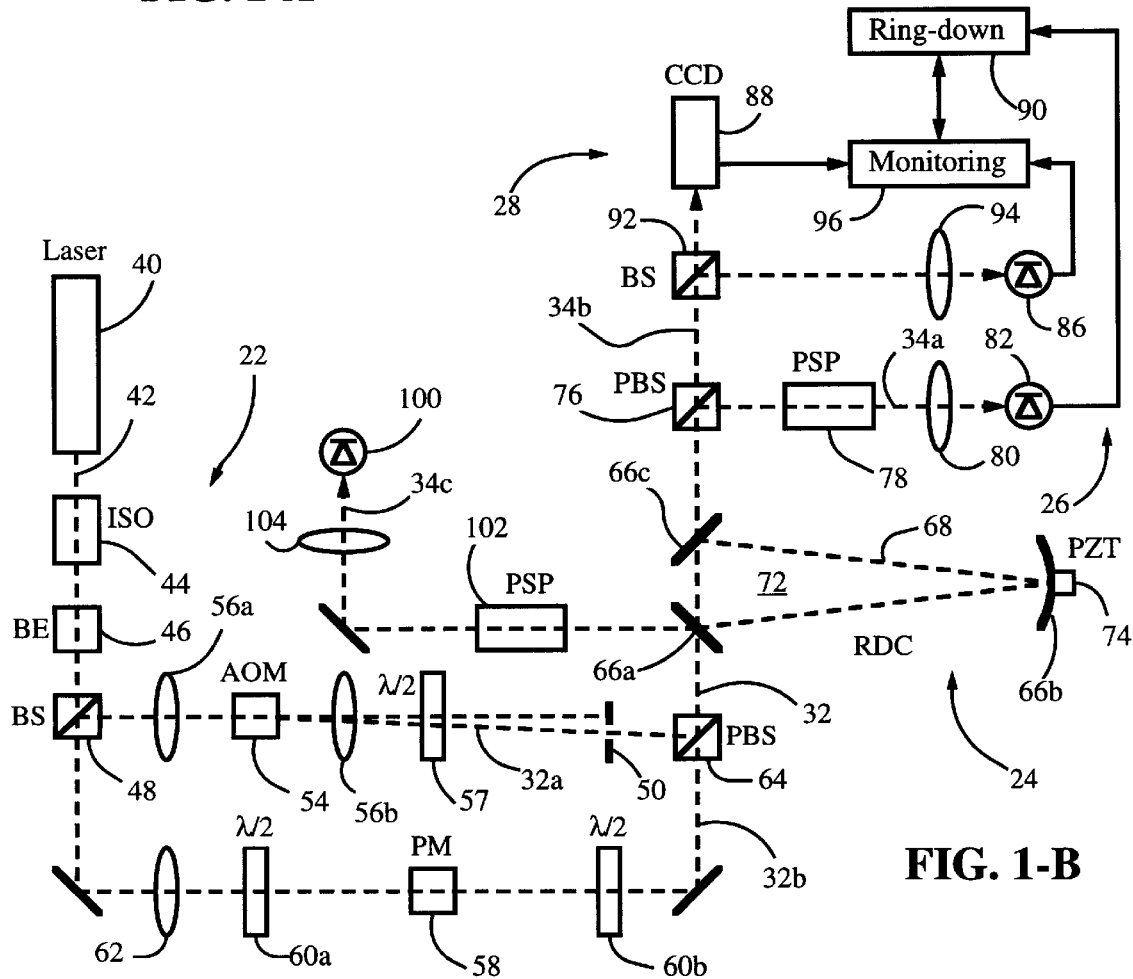
FIG. 1-B

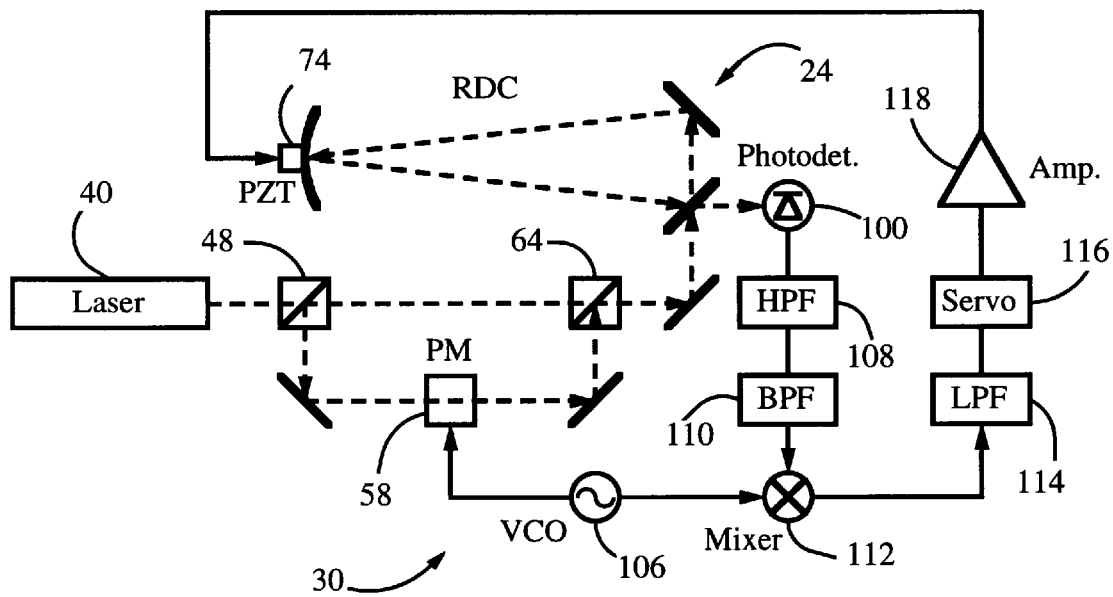
FIG. 1-C
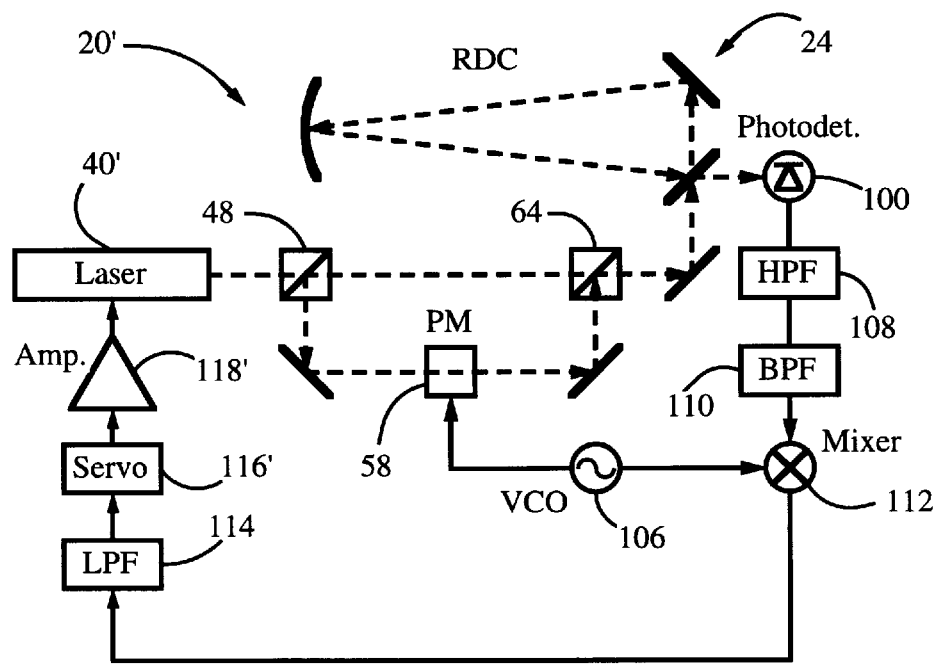
FIG. 2

CAVITY-LOCKED RING DOWN SPECTROSCOPY

RELATED APPLICATION DATA

This application is related to U.S. patent application ser. No. 08/879,975, filed Jun. 20, 1997 now U.S. Pat. No. 5,912,740, which is assigned to the assignee of the present invention.

U.S. GOVERNMENT RIGHTS

This invention was made with U.S. Government support under grant Nos. DE-FG03-92ER14304 awarded by the Department of Energy, and AF-F49620-97-1-0316 awarded by the Office of Scientific Research of the Air Force. The U.S. Government has certain rights in this invention.

BACKGROUND

This invention relates to cavity ring-down spectroscopy (CRDS), and in particular to systems and methods for locking a laser and a ring-down cavity for CRDS.

Traditional spectroscopic methods are limited in sensitivity to approximately one part per ten thousand ($1:10^4$) to one part per hundred thousand ($1:10^5$). Cavity Ring-Down Spectroscopy (CRDS), a technique first described by O'Keefe and Deacon in an article in Rev. Sci. Instrum.59(12) :2544–2551 (1988), allows one to make absorption measurements with sensitivities on the order of one part per ten million ($1:10^7$) to one part per billion ($1:10^9$) or higher.

In a conventional CRDS system, the sample (absorbing material) is placed in a high-finesse stable linear optical resonator. The intensity of a light pulse introduced in the resonator decreases in time. For an empty cavity, the intracavity light intensity follows an exponential decay characterized by a ring-down rate that depends only on the reflectivity of the mirrors, the separation between the mirrors, and the speed of light in the cavity. If a sample is placed in the resonator, the ring-down is accelerated. Under suitable conditions, the light decay remains exponential. An absorption spectrum for the sample is obtained by plotting the reciprocal of the ring-down rate versus the wavelength of the incident light.

Conventional pulsed CRDS systems have been faced with a number of challenges. In systems using pulsed lasers, data acquisition rates may be limited by the repetition rate of the pulsed laser source. Moreover, the intensity of the light coupled into and out of the cavity may be small, as a consequence of the relatively low spectral overlap between cavity modes and laser linewidth, as well as a lack of significant light buildup within the cavity.

In U.S. Pat. No. 5,528,040, Lehmann proposed the use of continuous-wave (c.w.) laser sources for CRDS, in particular laser diode (LD) sources. To improve the coupling of light into the ring-down cavity, Lehmann suggested optically locking the diode laser using controlled optical feedback from a reference cavity. The system described by Lehmann was subject to optical feedback from the ring-down cavity into the laser. Such optical feedback may cause instability in the laser operation. Moreover, locking was turned off during measurements, such that each measurement of a ring-down decay required re-locking the laser and cavity. Requiring that locking be turned off between measurements may limit the repetition rates achievable with the system.

OBJECTS AND ADVANTAGES

It is a primary object of the present invention to provide a system and method for stable and reliable locking of a laser and a ring-down cavity for CRDS. Another object is to provide a CRDS system allowing continuous locking of the laser and ring-down cavity over multiple ring-down measurements. It is another object to provide a CRDS system allowing high measurement repetition rates. It is yet another object to provide a CRDS system in which locking and sampling light have different frequencies, such that the locking light does not affect measurement values obtained using the sampling light. It is another object to provide a CRDS system with reduced shot-to-shot variation in the ring-down constant. Another object is to provide a CRDS system with reduced baseline noise. Still another object is to provide a CRDS system allowing locking of the laser and the ring-down cavity without requiring an external reference cavity. It is another object to provide a CRDS system allowing reduced optical feedback from the ring-down cavity to the laser. Yet another object is to provide a system allowing relatively simple coupling of locking light extending from the CRDS cavity to locking components.

SUMMARY

The present invention provides a CRDS system using distinct sampling and locking light beams. The sampling light is used for performing ring-down measurements, while the locking light is used for frequency-locking a ring-down resonant cavity and a c.w. laser. The locking light is maintained continuously on while the sampling light is turned on and off to allow obtaining ring-down measurements. Continuous locking allows higher measurement repetition rates, and consequently lower noise levels. The locking and sampling light have different frequencies such that the locking and sampling light are effectively decoupled within the cavity, ensuring that the locking light does not affect ring-down measurements performed with the sampling light.

In the preferred embodiment, the ring-down cavity is a ring-shaped cavity. For a given mode, the ring cavity has distinct resonant frequencies and mirror losses for s-polarized and p-polarized light. If intracavity losses are higher for p-polarized light than for s-polarized light, the sampling light is preferably s-polarized with respect to the cavity, while the locking light is p-polarized. The use of a ring-shaped cavity provides for a desirable separation between the resonant frequencies of a given mode, allowing tuning both the sampling and locking light to the same cavity mode without coupling the sampling and locking light. The use of a ring-shaped cavity provides the further advantage of allowing a reduction in optical feedback to the laser.

At least one of the locking and sampling light is frequency-shifted to ensure that the sampling and locking light are decoupled within the cavity. Preferably, an acousto-optic modulator (AOM) is positioned in the path of the sampling light. The AOM is used to introduce a difference between the frequencies of the sampling and locking light. The AOM is also used as a switch for turning the sampling light on and off to allow the performance of ring-down measurements.

In alternative embodiments, the ring-down cavity may be linear or folded. The sampling and locking light can then be tuned to the same transverse mode (e.g. $TEM_{00}$) corresponding to adjacent longitudinal modes. The frequency-shift between the sampling and locking light is then equal to one free spectral range of the cavity.

DESCRIPTION OF THE FIGURES

FIG. 1-A is a schematic high-level diagram of a preferred system of the present invention.

FIG. 1-B is a schematic diagram of the optical components of the system of FIG. 1-A.

FIG. 1-C illustrates the locking components of the system of FIG. 1-A.

FIG. 2 shows the locking components in an alternative embodiment of the present invention.

DETAILED DESCRIPTION

Figure 3:
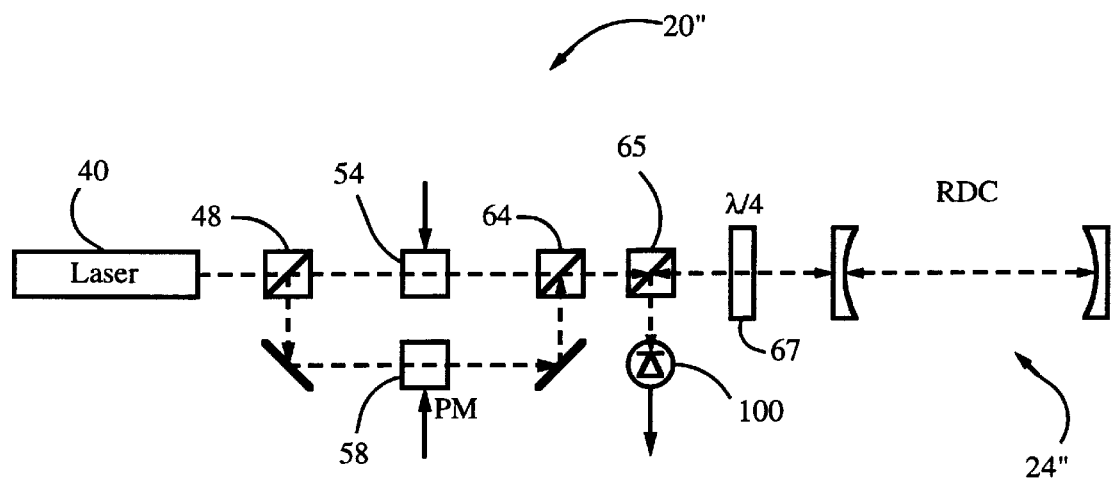
FIG. 3 shows an alternative embodiment of the present invention, using a linear ring-down cavity.

The following description illustrates the invention by way of example, and not necessarily by way of limitation. In the following discussion, unless otherwise stated, polarization directions will be understood to be considered relative to the ring-down resonant cavity of the system. Unless otherwise stated, the term "ring-down" is understood to encompass both decay and build-up (sometimes referred to as "ring-up") of light within the resonant cavity.

Preferred System

FIG. 1-A is a schematic high-level diagram of a preferred system 20 of the present invention. Optical connections are illustrated by dashed lines, while electrical connections are illustrated by solid lines. System 20 comprises a tunable monochromatic light source 22, a ring-down resonant cavity 24 in optical communication with light source 22, as well as sampling detection electronics 26, monitoring (diagnostics) electronics 28 and locking electronics 30 all in optical communication with cavity 24. Locking electronics 30 are electrically connected to light source 22 and cavity 24, while monitoring electronics 28 are electrically connected to sampling detection electronics 26.

Cavity 24 holds a sample of interest in an intracavity light path. Light source 22 generates c.w. input sampling light 32a and locking light 32b incident on cavity 24. Input sampling light 32a has a wavelength within an absorption region of interest of the sample. Input locking light 32b has a predetermined wavelength relationship with sampling light 32a. Sampling light 32a and locking light 32b have different frequencies within cavity 24. Preferably, sampling light 32a is s-polarized while locking light 32b is p-polarized.

Output light 34a–c extending from cavity 24 is incident on detection electronics 26, monitoring electronics 28, and locking electronics 30, respectively. Output light 34a–c comprises output sampling light 34a incident on sampling detection electronics 26, output monitoring light 34b incident on monitoring electronics 28, and output locking light 34c incident on locking electronics 30. Locking electronics 30 frequency-lock light source 22 and cavity 24, ensuring that the linewidth of intracavity sampling light overlaps the linewidth of a mode of interest of cavity 24. Sampling detection electronics 26 determine ring-down rates, absorption spectra, and species quantities for the sample of interest. Monitoring electronics 28 monitor the intensity and transverse mode structure of intracavity light. The intensity of intracavity light is used to characterize the locking of light source 22 and cavity 24. In one embodiment, measurements of peak intracavity light intensity are used to adjust the frequency separation between locking and sampling light.

FIG. 1-B illustrates the optics of system 20. Locking electronics 30 are illustrated in FIG. 1-C. For clarity of presentation, various standard elements such as lenses and mirrors used for focusing and directing beams are not described in detail; such elements are well known in the art.

Referring to FIG. 1-B, light source 22 comprises a continuous wave (c.w.) laser 40 for generating primary light 42, and optical components for generating input sampling light 32a and locking light 32b from primary light 42. Laser 40 preferably has a linewidth on the order of 1 MHz and a useful output power of at least 100 $\mu$W. Laser 40 is preferably a tunable external-cavity diode laser (ECDL). Other suitable light sources include solid state and dye lasers, as well as c.w. optical parametric oscillators (OPOs). Laser 40, including its controller, is mounted within a Faraday cage (not shown), for shielding laser 40 from stray electromagnetic interference which may otherwise cause instability in the temperature controller of laser 40.

An optical isolator 44 is positioned in the path of primary light 42, in optical communication with laser 40. Isolator 44 reduces the optical feedback caused by back reflections into laser 40, and controls the polarization of primary light 42. Isolator 44 is preferably a Faraday isolator including a half-wave plate adjusted to generate p-polarized light. A beam expander 46 and a beam splitter 48 are positioned in sequence in front of isolator 44, so as to receive light extending from isolator 44. Primary light 42 passes through beam expander 46 before being split by beam splitter 48 into sampling light 32a and locking light 32b.

An acousto-optic modulator (AOM) 54 is positioned in the path of sampling light 32a, between laser 40 and cavity 24. AOM 54 is driven by an RF signal generated by a voltage-controlled oscillator (not shown). AOM 54 is flanked by focusing and mode-matching optics 56a–b. Optics 56a comprise a mode-matching lens for selecting TEM$_{00}$ light for passage to cavity 24, and a focusing lens for collimating sampling light 32a onto AOM 54. Optics 56b comprise lenses for recollimating sampling light 32a after passage through AOM 54. A half-wave plate 57 is positioned in the path of sampling light 32a, for changing its polarization state to s-polarized. In the arrangement shown, AOM 54 is optimized for modulating p-polarized light, and thus half-wave plate 57 is positioned after AOM 54.

AOM 54 acts as a switch, for modulating (e.g. switching on and off) the intensity of sampling light 32a reaching cavity 24 so as to allow sampling light 32a to ring down within cavity 24.

AOM 54 may be used to generate pulses or continuous wave step inputs, among others. AOM 54 also acts as a frequency-shifter, for shifting the frequency of sampling light 32a incident on cavity 24 such that s-polarized sampling light 32a is tuned to a desired mode of cavity 24. AOM 54 shifts the frequency of sampling light 32a by an amount equal to the frequency of the RF signal driving AOM 54. Preferably, the first order beam from AOM 54 is directed to cavity 24. An aperture 50 is positioned in the optical path between AOM 54 and cavity 24, to select the first order beam from AOM 54 for passage to cavity 24 while blocking the zero order beam.

A phase-modulator (PM) 58 is situated in the path of locking light 32b, between laser 40 and cavity 24. PM 58 is preferably an electro-optic resonant phase modulator. In the particular arrangement shown, PM 58 is optimized for modulating s-polarized light, and is thus flanked by halfwave plates 60*a–b*. Half-wave plates 60*a–b* control the polarization of light within PM 58 so as to maximize the electro-optic effect within PM 58 for the particular crystal orientation of PM 58. PM 58 introduces locking sidebands into locking light 32*b*. The sidebands are separated from the central frequency $\omega_L$ of locking light 32*b* by a predetermined frequency separation $\omega_f$ larger than the linewidths of laser 40 and the mode of interest of cavity 24. The sideband at $\omega_L - \omega_f$ is phase-shifted by $\pi$ (180°) with respect to the sideband at $\omega_L + \omega_f$. A mode-matching lens 62 is situated in the path of locking light 32*b*, for selecting the $TEM_{00}$ mode for passage to cavity 24.

A polarizing beam splitter 64 is positioned in the paths of sampling light 32*a* and locking light 32*b*, facing cavity 24. Beam splitter 64 combines and directs sampling light 32*a* and locking light 32*b* toward cavity 24. Beam splitter 64, isolator 44, and half-wave plates 57, 60*a–b* act as polarization control elements, selecting s-polarized sampling light 32*a* and p-polarized locking light 32*b* for passage to cavity 24.

Cavity 24 comprises an input mirror 66*a*, an intermediate mirror 66*b*, and an output mirror 66*c*. Mirrors 66*a–c* define a closed, triangular intracavity light path 68. A gas sample 72 is situated within light path 68, and fills cavity 24. Sample 72 is an optically passive material (i.e. not a gain medium). Input mirror 66*a* and output mirror 66*c* are flat moderately-reflective mirrors. Intermediate mirror 66*b* is a highly-reflective spherical mirror. Intermediate mirror 66*b* is mounted on a piezoelectric stage 74. Stage 74 is used as a cavity pathlength control element. Stage 74 controls the position of mirror 66*b* relative to mirrors 66*a* and 66*c*, thus controlling the pathlength of cavity 24 and the resonant frequency of any given mode of cavity 24.

Preferably, the thermal expansion and stress tensor coefficients of cavity 24 are optimized so as to minimize cavity deformations (due to stretching, bowing, bending, etc.) and mechanical resonances. Therefore, it is preferred that the optical elements of cavity 24 are monolithically integrated. Mirrors 66*a,c* and stage 74 are rigidly attached to a common thermally stabilized block of material (not shown), preferably made of a low-thermal-expansion glass such as mica ceramic. The stable, monolithic attachment of mirrors 66*a,c* and stage 74 serves to reduce changes in the shape of cavity 24 due to mechanical vibrations and/or temperature variations. Such changes in shape could cause drift in the mode frequencies of cavity 24.

Input light 32*a–b* enters cavity 24 through input mirror 66*a* and generates an intracavity traveling wave along light path 68. Input light 32*a–b* is not normal to mirror 66*a*, such that light reflected by mirror 66*a* is not colinear with light incident on mirror 66*a*. The finesse of cavity 24 is high enough that the intracavity traveling wave propagates around cavity 24 multiple times. Intracavity locking (p-polarized) and sampling (s-polarized) light encounter different losses within cavity 24, and have different resonant frequencies for a given longitudinal mode of cavity 24. Detection light 34*a* and monitoring light 34*b* exit cavity 24 through output mirror 66*c*.

A polarizing beam splitter 76 is in optical communication with output mirror 66*c*. Beam splitter 76 is positioned in an optical path between mirror 66*c* and a sampling detector 82. Beam splitter 76 directs s-polarized sampling light 34*a* to sampling detector 82. Detector 82 is preferably a photodiode as described by Harb et al. in *Phys. Rev. A.* 54:4370 (1996), optimized to have a high gain. A polarization separator 78 and a focusing lens 80 are positioned in the optical path between beam splitter 76 and detector 82. Suitable polarization separators include Brewster windows, Glan-Taylor, Glan-Thomson, or Wollaston prisms, or Thomson beamsplitters, among others. Polarization separator 78 selects s-polarized sampling light 34*a* for transmission to sampling detector 82.

Ring-down electronics 90 are in electrical communication with sampling detector 82. Ring-down electronics 90 determine ring-down rates and corresponding absorption spectra for sample 72, by analyzing ring-down waveforms detected by sampling detector 82. Ring-down electronics 90 may also determine quantities of trace species of interest in sample 72. The intensity of output sampling light 34*a* incident on detector 82 is indicative of the intensity of sampling light within cavity 24, and thus of the interaction of sample 72 with intracavity sampling light. Ring-down electronics 90 are conventional. Ring-down electronics 90 may be implemented for example using computer software in an experimental setting, or using dedicated hardware in a process control device in a manufacturing setting.

Monitoring detectors 86, 88 are in optical communication with mirror 66*c*. Beam-splitter 76 directs p-polarized monitoring light 34*b* to monitoring detectors 86, 88, through a beam splitter 92 and a focusing lens 94. Detector 86 is preferably a photodiode as described in the above-referenced article by Harb et al. Detector 86 is used to monitor the power of intracavity light. Detector 86 may be connected through monitoring servo electronics (not shown) to AOM 54, for adjusting the driving frequency of AOM 54 to compensate for changes in the frequency difference between sampling and locking resonances. Such changes may be caused by sample dispersion.

Detector 88 is preferably a charge-coupled-device array (CCD camera). Detector 88 is used to monitor the transverse mode structure of intracavity light, ideally to ascertain that only $TEM_{00}$ light propagates within cavity 24. Monitoring processing electronics 96 are in electrical communication with detectors 86 and 88, and with ring-down electronics 90. Electronics 96 communicate recorded monitoring data to ring-down electronics 90 for storage with corresponding ring-down data.

A locking detector 100 is in optical communication with input mirror 66*a*, and is positioned to capture output locking light 34*c* extending from input mirror 66*a*. Locking detector 100 is preferably a photodiode similar to that used for monitoring detector 86, optimized for high bandwidth in order to render the locking sidebands with minimal distortion and noise. A polarization separator 102 and a focusing lens 104 are positioned in an optical path of locking light 34*c*, between mirror 66*a* and locking detector 100. Light extending from input mirror 66*a* consists of a reflected component reflected by input mirror 66*a*, and of a leakage component transmitted through input mirror 66*a* from cavity 24. Polarization separator 102 selects p-polarized locking light 34*c* for transmission to detector 100.

Detector 100 is part of locking electronics 30. FIG. 1-C shows a schematic diagram of locking electronics 30. The design of locking electronics 30 is based on the Pound-Drever locking system. For detailed information on Pound-Drever locking see the article by Drever et al. in *Appl. Phys. B* 31:97–105 (1983).

Referring to FIG. 1-C, a high-pass filter (HPF) 108 is electrically connected to the output of detector 100. The pass-threshold of HPF 108 is less than the frequency separation $\omega_f$ between the central frequency and the locking sidebands of the signal detected by detector 100. A bandpass filter (BPF) 110 is connected to the output of HPF 108. The passband of EPF 110 is centered at $\omega_f$. The output of BPF 110 is connected to an input of a mixer 112. Another input of mixer 112 is connected to a first output of a voltage-controlled oscillator (VCO) 106 capable of generating a driving signal at the frequency $\omega_f$. A second output of VCO 106 is connected to PM 58, for driving PM 58. An output of mixer 112 is connected to a low-pass filter (LPF) 114. The pass-threshold of LPF 114 is less than $2\omega_f$. The output of LPF 114 is connected to servo electronics 116, which are in turn connected through an amplifier 118 to stage 74.

VCO 106 generates a driving signal at $\omega_f$ for driving PM 58. PM 58 inserts locking sidebands into locking light 32b at frequencies $\omega_L \pm \omega_f$, where $\omega_L$ is the frequency of the central band of locking light 32b. Output locking light 34c is formed by the reflection of locking light 32b and the locking light leaking from cavity 24. The amplitudes of the sidebands of locking light 34c depend on the tuning of each sideband to cavity 24, and consequently on the difference between $\omega_L$ and the corresponding resonant frequency of a given mode of interest of cavity 24. For example, if $\omega_L$ is higher than a corresponding resonant frequency of cavity 24, the reflected sideband at $\omega_L - \omega_f$ has a lower intensity than the reflected sideband at $\omega_L + \omega_f$.

Locking light 34c detected by detector 100 includes a frequency component at $\omega_L$ and a frequency component at $\omega_f$. Typically, $\omega_L$ is on the order of $10^{14}$ Hz, while $\omega_f$ is on the order of $10^7$ Hz. Detector 100 is not fast-enough to time-resolve the $\omega_L$ component of locking light 34c. Consequently, the electric signal generated by detector 100 includes a component centered at zero frequency, corresponding to the $\omega_L$ frequency component of locking light 34c. Detector 100 can time-resolve the $\omega_f$ component of locking light 34c, and thus the generated electric signal includes a component centered at $\omega_f$. HPF 108 and BPF 110 select the $\omega_f$ frequency component for passage to mixer 112.

Mixer 112 mixes the signals received from VCO 106 and detector 100 to generate an error signal centered at zero frequency. Mixer 112 effectively differences the sideband signals to generate the error signal. The sign of the error signal indicates whether $\omega_L$ is higher or lower than the corresponding resonant frequency of cavity 24. LPF 114 eliminates higher-harmonics (e.g. $2\omega_f$) from the signal generated by mixer 112, selecting the zero-frequency error signal for passage to servo electronics 116. Servo electronics 116 translate the error signal into an appropriate motion of stage 74, for adjusting the pathlength and thus resonant frequency of interest of cavity 24 to ensure that a desired mode of cavity 24 is tuned to $\omega_L$.

Locking light 32b is continuously turned on during the operation of system 20, for ensuring continuous locking of cavity 24 and light source 22. Sampling light 32a is selectively turned off after sufficient accumulation of light within cavity 24 during periods of c.w. operation, to allow measurements of the ring-down of sampling light 32a within cavity 24. Maintaining locking light 32b turned on while performing multiple ring-down measurements allows relatively high repetition rates (e.g. kHz to tens of kHz) for system 20.

Alternative Systems

FIG. 2 is a simplified diagram illustrating an alternative system 20' according to the present invention. Locking electronics 30' control the frequency of light emitted by a laser 40', so as to tune the central band of locking light 32b to cavity 24. The output of mixer 112 is connected through LPF 114, servo electronics 116', and an amplifier 118' to a frequency controller of laser 40'. If $\omega_L$ is higher than the resonant frequency of interest of cavity 24, servo electronics 116' control laser 40' to reduce its emission frequency so as to tune $\omega_L$ to the desired mode of cavity 24. Similarly, $\omega_L$ is increased if it is lower than desired.

FIG. 3 is a simplified diagram illustrating another alternative system 20" of the present invention. System 20" includes a linear ring-down cavity 24". A polarizing beam splitter 65 and a quarter-wave plate 67 are positioned in sequence between PBS 64 and cavity 24", in the optical path of the sampling and locking light. PBS 65 directs incident locking and sampling light toward cavity 24", while directing reflected locking light toward detector 100. The frequencies of the sampling and locking light are tuned to the same transverse mode (e.g. $TEM_{00}$) but different (e.g. adjacent) longitudinal modes of cavity 24". The frequency difference between the sampling and locking light is equal to one free spectral range (FSR) of cavity 24". For typical FSR values of hundreds of MHz, a conventional AOM is well suited for introducing the desired frequency difference between the sampling and locking light.

Discussion

Baseline noise in CRDS is caused in large part by concurrent excitation and beating of multiple modes within the ring-down cavity (RDC), or by consecutive excitation of different modes. Different transverse/longitudinal modes have different resonant frequencies, and ring-down at different rates in an empty cavity. Ensuring that a single mode is excited within the ring-down cavity allows a significant improvement in system signal-to-noise ratios.

Because frequency fluctuations in the laser source appear identically in both sampling and locking light, if a locking light mode is locked to the cavity, then a corresponding sampling light mode is also locked to the cavity. The AOM used for switching the sampling light on and off provides the appropriate frequency shift to the sampling light, so that it can couple into the same transverse mode as the locking light.

Using a ring-shaped ring-down cavity in a system of the present invention provides a number of advantages. The use of a ring-shaped cavity provides for the desired separation between the resonant frequencies for sampling and locking light of different polarizations, allows a simplification in the optics used for coupling locking light into and out of the cavity, and allows a reduction in optical feedback to the laser.

It is generally well-known from the physics of optical interfaces that non-normal incidence of linearly polarized light on a dielectric interface will usually result in different responses for p-polarized light (PPL) and s-polarized light (SPL). Thus, an optical ring resonator constructed with a geometry using non-normal incidence reflectors (e.g., an isosceles triangle) will actually consist of two superimposed nondegenerate Fabry-Perot cavities: a p-polarization cavity (PPC), and an s-polarization cavity (SPC).

Non-normal incidence dielectric mirrors typically have a lower reflectivity for PPL than they do for SPL. Consequently, a ring resonator will usually consist of a reduced finesse PPC, and a higher finesse SPC. The ring resonator PPC and SPC transverse mode structures are identical, because they are determined only by geometrical considerations. The unequal phase shifts accrued during non-normal reflection of PPL and SPL will result in a fixed frequency difference between the PPC and SPC frequency responses. PPC and SPC free spectral ranges differ by the contribution of the derivative of the mirror phase shift, which was estimated to be a few tens of kHz.

Because orthogonal polarizations are easily separated with polarizing optics, the simultaneous use of PPL and SPL provides a straightforward solution for separating the cavity locking problem from the actual ring-down measurement. The use of the lower finesse PPC for locking improves the feedback locking signal, and relaxes requirements on servo bandwidth, feedback gain, and differential sensitivity to the frequency difference between the laser and cavity. Absolute wavelength accuracy at each point is determined by the PPC finesse and locking servo quality, rather than by laser linewidth or cavity mode sweep range. The improved frequency stability enables a substantial increase in the resolution achievable with such a system.

The use of a ring cavity also allows a significant simplification in the optics used to couple locking light into locking components. In a system using a linear or folded cavity, the optical signal extending from the cavity input is colinear with the light beam incident on the cavity input. As a result, optical components such as half-wave plates, analyzers, and beam-splitters may be needed to selectively couple the locking light reflected by the cavity input into the locking electronics. Furthermore, ring cavities do not reflect light directly back into the light source, so that optical feedback problems are greatly reduced.

The following example is intended to illustrate a particular implementation of the invention, and should not be construed to limit the invention.

EXAMPLE

A system of the present invention was used to generate spectra of water vapor in ambient air. The laser was a commercial ECDL (New Focus: 6226-H032), tunable from 833.2 nm to 862.5 nm. The laser output varied from about 9 to 13 nW for 60 mA drive current, over the entire tuning range. A 25–35 dB Faraday isolator (New Focus: 5568) was used to reduce residual back reflections into the laser. The input and output mirrors of the RDC (CVI:TLM2-800-45S-1037) had 99.93% reflectivity for SPL at 833 nm, and 99.3% reflectivity for PPL at 833 nm. The intermediate RDC mirror (REO: run C628, 7.75 mm, 840–880 nm, 1 degree wedge) had a 99.95% reflectivity at 833 nm for both polarizations.

One quarter of the primary light generated by the laser was used for locking and three quarters for sampling. The input sampling light was focused to a spot size of 60 $\mu$m at the center of the AOM (Brimrose: GPM-400-100-960), and recollimated using 5 cm focal length lenses. The AOM was driven by a VCO with a frequency range of 300 to 535 MHz. The AOM imparted a frequency shift of 320 MHz to the input sampling light. The lenses used for $TEM_{00}$ mode-matching of the sampling and locking light had a focal length of 127 cm. The phase modulator was a 58.5 MHz electro-optic resonant phase modulator (New Focus:4001). The fraction of laser light coupled into the $TEM_{00}$ mode of the cavity was ~90% for PPL, and ~85% for SPL.

The VCO driving the phase-modulator was set to 58.5 MHz. A Glan-Taylor prism was used to select PPL for passage to the locking detector. The bandpass of the locking bandpass filter was centered at 60 MHz. The servo electronics consisted of a proportional integral (PI) controller coupled to a passive notch filter centered at 52 kHz (48 dB maximum attenuation, 3 dB bandwidth of 2 kHz). The notch filter was used to suppress oscillation of the piezoelectric stage at its resonant frequency of 52 kHz. The use of the notch filter improved the stability of the system and reduced its sensitivity to external perturbations such as acoustic noise. The gain of the servo electronics and associated amplifier was 60 dB, with a 3 dB bandwidth of 455 Hz.

The locking and monitoring photodiodes were optimized for a bandwidth of 90 MHz. Shot-noise-limited sideband signals were readily attainable for optical powers of hundreds of $\mu$W at the detectors. The sampling photodiode was optimized for gain, at a bandwidth of 25 MHz. The output sampling light power was on the order of $\mu$W, and the detected ring-down decay constants were on the order of hundreds of ns or higher. The monitoring photodiode received 90% of the monitoring light, while the monitoring CCD camera received the remaining 10%.

A Glan-Thomson prism was used to select SPL for passage to the sampling detector. After detection by the sampling detector, the sampling signals were amplified using a low-noise, high-speed amplifier (Stanford Research Systems:SR445), and digitized using a 10-bit, 1 GHz oscilloscope (Tektronix:11402). The decay waveforms were fitted using the Levenberg-Marquardt algorithm with the initial guess provided by a linear least squares fit of the signal logarithm, as described by Naus et al. in *ILS-XII 12th Interdisciplinary Laser Science Conference*. ed. A. P. Society (OSA, Rochester, N.Y. 1996), p. 122. All scans were performed in air at atmospheric pressure, with a water partial pressure of 12 torr.

Figure 4:
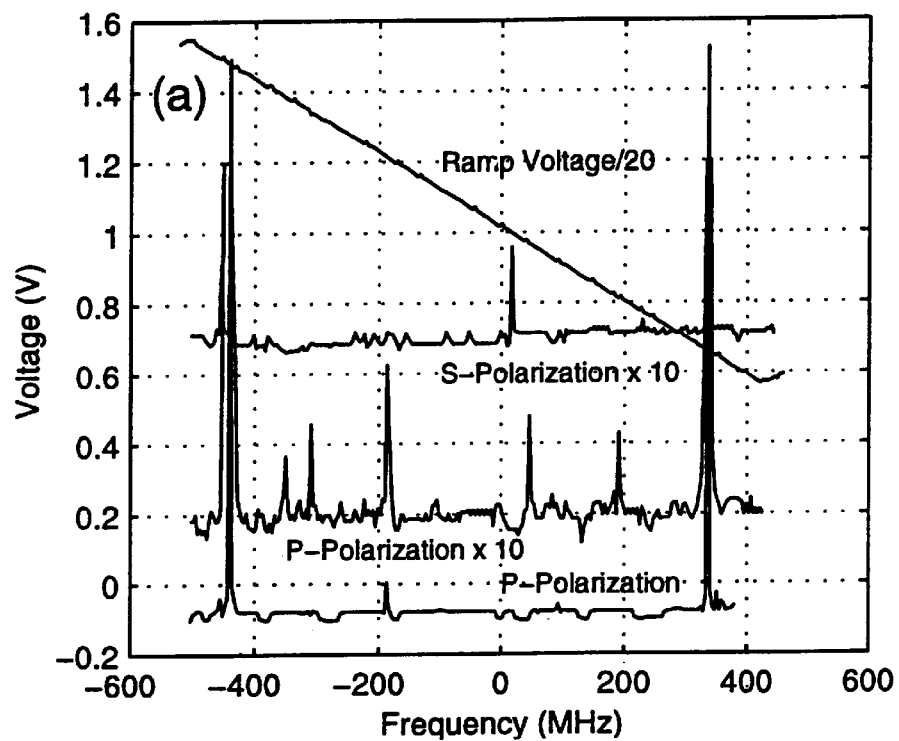
FIG. 4 shows scans of the cavity frequency response for p-polarized light and s-polarized light for an exemplary system of the present invention.

FIG. 4 shows scans of the cavity frequency response for PPL and SPL. The zero frequency is arbitrary. The resonance frequencies for SPL and PPL were observed to be separated by 282 MHz. The resonance frequency separation changed by several tens of kHz when the cavity modes overlapped an absorption line of water. The driving frequency for the AOM was accordingly adjusted using intensity information from the monitoring electronics, to maintain an appropriate frequency separation between the locking and sampling light. For small sample quantities (e.g. for trace species detection), the frequency separation resulting from dispersion by the sample is generally small or negligible.

Figure 5:
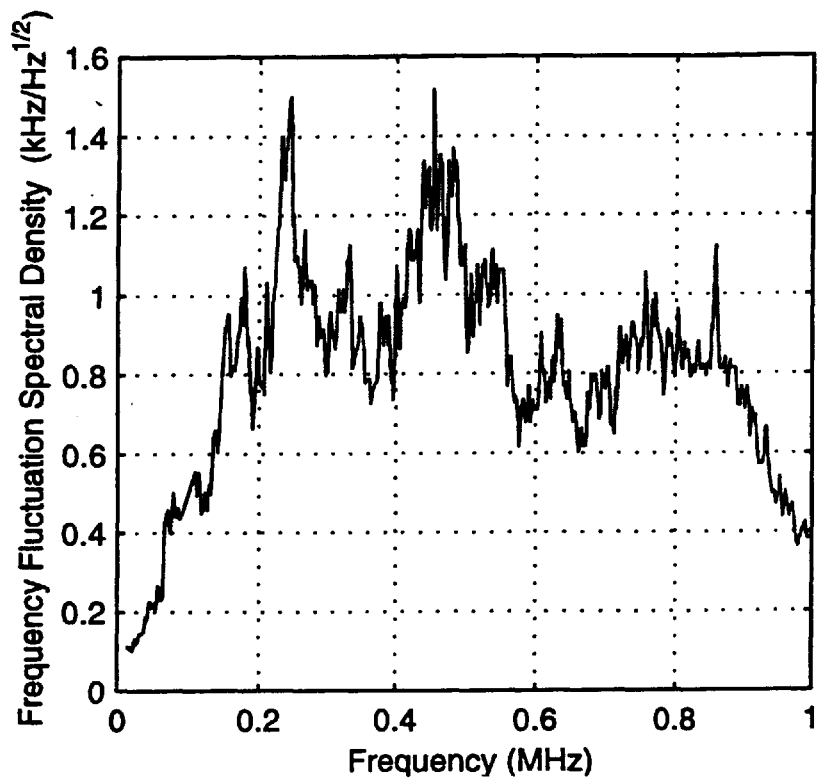
FIG. 5 shows a measured plot of the spectral density of the frequency difference fluctuation as a function of frequency difference for the exemplary system characterized by FIG. 4.

The discriminator slope of the error signal generated by the mixer, which converts error signal voltage into frequency difference, was used to determine fluctuations in the frequency difference between the laser frequency and the cavity resonance frequency. FIG. 5 shows a measured plot of the spectral density of the frequency difference fluctuation (noise as a function of frequency difference between the laser and cavity). The total jitter between the laser and cavity resonances was 1.1 MHz, slightly less than the free-running laser linewidth. The locking components reduced noise at low frequencies (<20 kHz). Faster servo electronics may generally be used for reducing higher frequency components of the noise.

Figure 6:
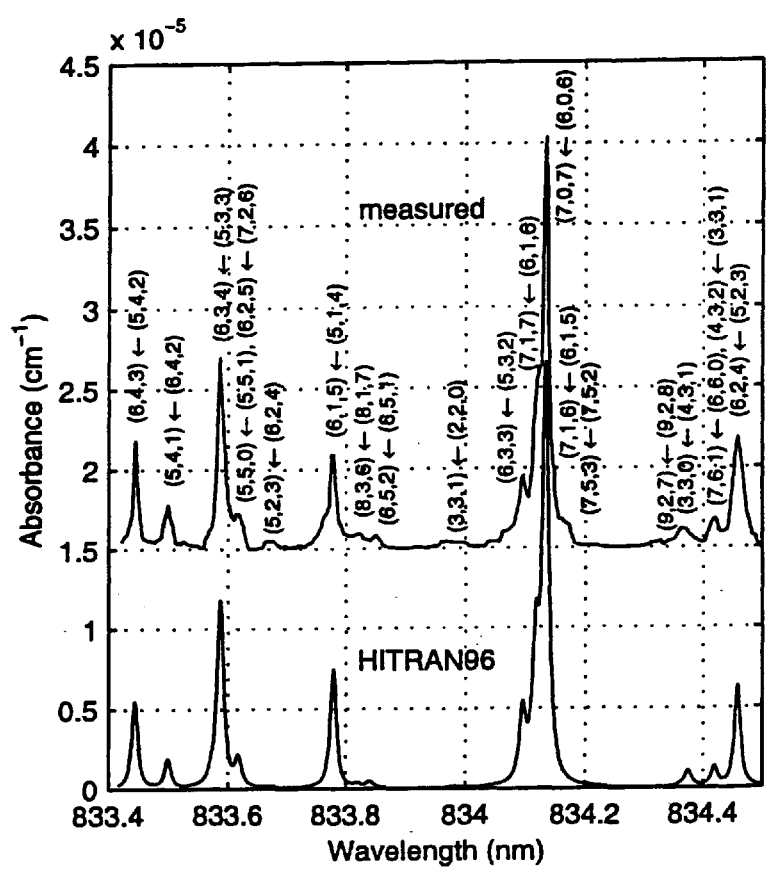
FIG. 6 shows a spectrum of water vapor in ambient room air recorded using the exemplary system characterized by FIG. 4.

FIG. 6 shows a spectrum of water vapor in ambient room air recorded using the system described above, and a corresponding spectrum obtained from the HITRAN96 database. The resolution of the recorded spectrum was 0.002 nm, except about the absorption peaks where the resolution was increased to 0.001 nm. Ten averaged decay waveforms (ADW) were recorded at each wavelength. Each ADW was determined by averaging 256 shots. The RMS baseline noise was $5 \times 10^{-9}$ cm$^{-1}$, and the nominal sensitivity was 5 ppm. The recorded spectrum compares favorably to the HITRAN96 spectrum in absolute frequency, linestrength, and linewidth.

It will be clear to one skilled in the art that the above embodiments may be altered in many ways without departing from the scope of the invention. For example, a system of the present invention may be used for applications in a wide variety of wavelength ranges, and for characterizing a variety of species of interest. Various locking schemes and electronics may be used. Accordingly, the scope of the invention should be determined by the following claims and their legal equivalents.

What is claimed is:

1. A cavity ring-down spectroscopy system comprising:
   a) a ring-down ring resonant cavity for holding a sample;
   b) a light source comprising a laser in optical communication with said cavity, for generating a locking light and a sampling light incident on said cavity, wherein one of said locking light and said sampling light is s-polarized within said cavity, and the other of said locking light and said sampling light is p-polarized within said cavity;
   c) locking electronics in optical communication with said cavity for receiving said locking light reflected by said cavity and for locking said cavity and said light source using said locking light reflected by said cavity; and
   d) sampling electronics in optical communication with said cavity, for detecting said sampling light extending from said cavity and for determining ring-down rates indicative of an absorption of said sampling light by said sample.

2. The system of claim 1 wherein said light source further comprises polarization control optics in an optical path between said laser and said cavity, for selecting a p-polarization for said locking light, and for selecting an s-polarization for said sampling light.

3. The system of claim 1 wherein said light source further comprises frequency-shifting optics in an optical path between said laser and said cavity, for frequency-shifting at least one of said locking light and said sampling light to tune said at least of said locking light and said sampling light to a predetermined mode of said cavity.

4. The system of claim 1 wherein said light source further comprises an acousto-optic modulator positioned in an optical path of said sampling light between said laser and said cavity, for frequency-shifting said sampling light to tune said sampling light to said cavity, and for switching said sampling light to allow said sampling light to ring down within said cavity.

5. The system of claim 1 wherein said cavity comprises a cavity pathlength control element in electrical communication with said locking electronics, for controlling an optical pathlength of said cavity to lock said cavity to said light source.

6. The system of claim 1 wherein said locking electronics comprise:
   a) a locking detector in optical communication with said cavity, for detecting said locking light reflected by said cavity; and
   b) processing electronics in electrical communication with said locking detector, for generating an error signal indicative of a difference between a central frequency of said locking light and a resonant frequency of said cavity.

7. The system of claim 6 wherein:
   a) said light source further comprises a phase modulator in an optical path of said locking light between said laser and said cavity; and
   b) said locking electronics further comprise
      an oscillator in electrical communication with said phase modulator, for driving said phase modulator to insert a first and a second sideband in said locking light, said first sideband being at a higher frequency than said central frequency, said second sideband being at a lower frequency than said central frequency, and
      a mixer in electrical communication with said locking detector and said oscillator, for differencing electrical signals corresponding to said first sideband and said second sideband to generate said error signal.

8. The system of claim 1 wherein said laser is selected from the group consisting of diode lasers, solid-state lasers and quantum-cascade lasers.

9. A cavity ring-down spectroscopy system comprising:
   a) a ring-down spectroscopy ring resonant cavity for holding a sample, said cavity having an input and an output;
   b) a continuous-wave tunable laser in optical communication with said input, for generating a primary light beam;
   c) beam splitting optics in an optical path between said laser and said input, for splitting said primary light beam into a locking light beam incident on said input and a sampling light beam incident on said input, said locking light beam being p-polarized and said sampling light beam being s-polarized within said cavity;
   d) locking electronics in optical communication with said input for generating an electric feedback error signal from a reflection of said locking light beam from said input, and for locking said laser and said cavity using said error signal;
   e) a switch positioned between said beam splitting optics and said input, in an optical path of said sampling light beam, for switching said sampling light beam to allow said sampling light beam to ring down within said cavity multiple times while said laser and said cavity are locked;
   f) a sampling detector in optical communication with said output, for detecting said sampling light beam transmitted by said cavity; and
   g) ring-down electronics in electrical communication with said detector, for determining a ring-down rate for said sampling light beam.

10. A cavity ring-down spectroscopy system comprising:
    a) a ring-down ring resonant cavity for holding a sample;
    b) a light source;
    c) optics between said light source and said cavity for deriving from said light source a locking light and a sampling light and for simultaneously in-coupling said locking light and said sampling light into said cavity, said locking light having a different frequency than said sampling light;
    d) locking electronics in optical communication with said cavity for locking said cavity and said light source using said locking light reflected by said cavity; and
    e) a sampling detector in optical communication with said cavity, for detecting a plurality of ring-downs of said sampling light extending from said cavity while said cavity and said light source are locked.

11. The system of claim 10 wherein a frequency separation between said sampling light and said locking light is substantially equal to one free spectral range of said cavity.

12. The system of claim 10 wherein said light source comprises a continuous-wave tunable laser for generating a primary light beam, and said optics comprise:
    a) beam splitting optics in an optical path between said laser and said cavity, for splitting said primary beam into said locking light and said sampling light; and b) frequency-shifting optics positioned in an optical path of at least one of said sampling light and said locking light, for frequency-shifting said at least one of said sampling light and said locking light.

13. The system of claim 12 wherein said frequency-shifting optics comprise an acousto-optic modulator positioned in a path of said sampling light.

14. A cavity ring-down spectroscopy system comprising:
a) a ring-down resonant cavity for holding a sample;
b) a light source;
c) optics between said light source and said cavity for deriving from said light source a locking light and a sampling light and for simultaneously in-coupling said locking light and said sampling light into said cavity, said locking light having a different frequency than said sampling light;
d) locking means in optical communication with said cavity, for locking said cavity and said light source using said locking light reflected by said cavity;
e) detection means in optical communication with said cavity, for detecting multiple ring-downs of said sampling light extending from said cavity while said cavity and said light source are locked; and
f) ring-down means in electrical communication with said detection means, for determining ring-down rates of said ring-downs.

15. The system of claim 12 wherein said cavity is a ring-shaped cavity.

16. The system of claim 15 wherein:
a) one of said locking light and said sampling light is s-polarized within said cavity; and
b) the other of said locking light and said sampling light is p-polarized within said cavity.

17. The system of claim 14 wherein said cavity is a linear cavity.

18. The system of claim 17 wherein a frequency separation between said sampling light and said locking light is substantially equal to one free spectral range of said cavity.

19. A method of locking a laser and a cavity for ring-down spectroscopy, comprising the steps of:
a) using said laser to generate a light beam;
b) using optics to derive from said light beam a sampling light and a locking light and simultaneously in-coupling said sampling light and said locking light into said cavity, wherein said sampling light and said locking light have different frequencies;
c) using said locking light to lock said cavity and said laser; and
d) obtaining a plurality of measurements of a ring-down of said sampling light while maintaining said cavity and said laser in a locked state, for generating an absorption spectrum of a sample situated within said cavity.

* * * * *